US010549031B2

(12) United States Patent
Imran (10) Patent No.: US 10,549,031 B2
(45) Date of Patent: Feb. 4, 2020

(54) INFUSION SYSTEM FOR THE CONTROLLED DELIVERY OF THERAPEUTIC AGENTS

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 376 days.

(21) Appl. No.: 15/462,602

(22) Filed: Mar. 17, 2017

(65) Prior Publication Data
US 2017/0281858 A1     Oct. 5, 2017

Related U.S. Application Data

(63) Continuation of application No. 14/208,520, filed on Mar. 13, 2014, now Pat. No. 9,597,449.
(Continued)

(51) Int. Cl.
*A61M 5/145* (2006.01)
*A61M 5/148* (2006.01)
*A61M 5/142* (2006.01)

(52) U.S. Cl.
CPC ........ *A61M 5/14593* (2013.01); *A61M 5/148* (2013.01); *A61M 5/1483* (2013.01);
(Continued)

(58) Field of Classification Search
CPC ............ A61M 5/1483; A61M 5/14586; A61M 5/14593; A61M 5/155; A61M 5/16804;
(Continued)

(56) References Cited

U.S. PATENT DOCUMENTS 3,298,367 A     1/1967   Bergman
3,877,428 A     4/1975   Seagle et al.
(Continued)

FOREIGN PATENT DOCUMENTS

CA     1125134     6/1982
EP     0217940     4/1987
(Continued)

OTHER PUBLICATIONS

U.S. Appl. No. 14/208,520, Non-Final Office Action dated Feb. 10, 2016, 12 pages.
(Continued)

*Primary Examiner* — Andrew M Gilbert
(74) *Attorney, Agent, or Firm* — Kilpatrick Townsend & Stockton LLP (57) ABSTRACT

Embodiments of the invention provide infusion systems for the intravenous or other delivery of drugs and other therapeutic agents to a patient including a human or mammal. The therapeutic agents may be dissolved in solution or comprise the solution itself. Embodiments of the systems can utilize a chemical reaction to predictably drive a flow of drug(s) through a catheter or other flow path and into the patient. More specifically, the reaction may include an acid-base reaction or any other reaction that produces a gaseous substance. The gas is produced and contained in an expandable drive balloon when the acid-base reactants are combined with a liquid. As the gas is produced, the drive balloon expands to exert pressure on a separately-contained drug reservoir which, in turn, pushes drug(s) from the reservoir into the flow path where the drug is ultimately delivered to the patient in a controlled and predetermined manner.

25 Claims, 9 Drawing Sheets

Related U.S. Application Data (60) Provisional application No. 61/779,817, filed on Mar. 13, 2013.

(52) U.S. Cl.
CPC .............. *A61M 2005/14204* (2013.01); *A61M 2205/3389* (2013.01); *A61M 2205/3561* (2013.01); *A61M 2205/3569* (2013.01); *A61M 2205/3576* (2013.01)

(58) Field of Classification Search
CPC .... A61M 5/16881; A61M 2005/14204; A61M 2005/14513
See application file for complete search history.

(56) References Cited

U.S. PATENT DOCUMENTS

| | | | |
|---|---|---|---|
| 4,175,558 A | 11/1979 | Hess, III et al. | |
| 4,379,453 A | 4/1983 | Baron | |
| 5,013,303 A | 5/1991 | Tamari et al. | |
| 5,019,055 A | 5/1991 | O'Boyle | |
| 5,106,374 A | 4/1992 | Apperson et al. | |
| 5,135,498 A * | 8/1992 | Kam | A61M 5/1483 128/DIG. 12 |
| 5,318,515 A | 6/1994 | Wilk | |
| 5,318,540 A | 6/1994 | Athayde et al. | |
| 5,348,539 A | 9/1994 | Herskowitz | |
| 5,398,851 A * | 3/1995 | Sancoff | A61M 5/14593 222/386.5 |
| 5,492,534 A | 2/1996 | Athayde et al. | |
| 5,700,245 A | 12/1997 | Sancoff et al. | |
| 5,707,499 A | 1/1998 | Joshi et al. | |
| 5,738,657 A | 4/1998 | Bryant et al. | |
| 5,891,097 A | 4/1999 | Saito et al. | |
| 6,280,416 B1 | 8/2001 | Van Antwerp et al. | |
| 6,428,505 B1 | 8/2002 | Taylor | |
| 6,520,936 B1 | 2/2003 | Mann | |
| 7,540,851 B2 * | 6/2009 | O'Mahony | A61M 1/3653 604/6.09 |
| 8,257,337 B2 | 9/2012 | Ross | |
| 9,597,449 B2 * | 3/2017 | Imran | A61M 5/1483 |
| 2003/0009132 A1 * | 1/2003 | Schwartz | A61M 5/158 604/152 |
| 2004/0073169 A1 | 4/2004 | Amisar et al. | |
| 2005/0065466 A1 * | 3/2005 | Vedrine | A61M 5/14248 604/93.01 |
| 2006/0079862 A1 | 4/2006 | Genosar | |
| 2010/0076413 A1 | 3/2010 | Imran | |
| 2010/0179473 A1 * | 7/2010 | Genosar | A61M 5/14248 604/70 |
| 2012/0267275 A1 | 10/2012 | Gilmore | |
| 2013/0237915 A1 * | 9/2013 | Barrelli | A61M 5/14244 604/136 |
| 2014/0276587 A1 | 9/2014 | Imran | |

FOREIGN PATENT DOCUMENTS

| | | |
|---|---|---|
| EP | 265261 | 4/1988 |
| EP | 0462213 | 12/1991 |
| WO | 8605993 | 10/1986 |
| WO | 9010467 | 9/1990 |

OTHER PUBLICATIONS

U.S. Appl. No. 14/208,520, Notice of Allowance dated Nov. 8, 2016, 12 pages.
International Application No. PCT/US2014/026314, International Search Report and Written Opinion dated Jul. 4, 2014, 18 pages.

\* cited by examiner

INFUSION SYSTEM FOR THE CONTROLLED DELIVERY OF THERAPEUTIC AGENTS

RELATED APPLICATIONS

This application is a continuation of U.S. patent application Ser. No. 14/208,520, now U.S. Pat. No. 9,597,449, entitled "Infusion System for the Controlled Delivery of Therapeutic Agents", filed Mar. 13, 2014, which claims the benefit of priority to Provisional U.S. Patent Application No. 61/779,817, entitled "Infusion Systems for the Controlled Delivery of Therapeutic Agents", filed Mar. 13, 2013; the full disclosures of which are incorporated herein by reference in their entirety for all purposes.

BACKGROUND OF THE INVENTION

Infusion systems, including intravenous (IV) delivery of fluids and drugs, have been used for nearly 200 years. Today, infusion systems remain a fundamental and integral part of the routine care of patients, especially those undergoing chemotherapy, anesthesia, blood transfusions, insulin therapy, and fluid or electrolyte replacement. Systems to control the subcutaneous or even transdermal delivery of therapeutic agents are also commonly used, particularly to manage chronic pain, for example. However, inappropriate IV therapy remains a significant cause of patient morbidity and mortality most commonly resulting from administration of an incorrect volume (e.g. over or under delivery of the desired drug dosage) and/or administration of an incorrect fluid or drug. Drugs are delivered to the site of action extremely rapidly with IV injection and the effects are often experienced in as little as 10 seconds after dosing. Thus, there is a high risk of overdose if the dose has been calculated incorrectly. There is also an increased risk of deleterious side effects if the drug is administered too rapidly.

During administration, invariably there is a need for dosing therapeutic agents at constant and/or predetermined flow rates. In addition to providing a basal infusion rate (i.e. maintenance IV fluids), it is desirable that these medications are carried into the cannulated vein by a continuous IV flow. Administration of excess quantities of IV fluids is wasteful, undesirable and often harmful to the patient causing conditions such as edema. In addition to the above, the need to mix therapeutic agents with an IV solution invites human error including the potential to provide an incorrect mixture of drugs and/or an incorrect dosage of drugs to the patient. This is particularly the case during various surgical and/or emergency medical procedures where there is often a need to quickly administer various drugs and/or IV fluids.

The most commonly used IV infusion system consists of a bag filled with fluids, a drip chamber, roller clamp (i.e. variable resistance controller) for control of the flow and tubing connected to an IV catheter. The elevated IV bag in this system serves as a pressure source, the roller clamp as a user-controlled resistor, and the IV catheter as a fixed resistor.

Most commonly, the rate of IV fluids flow is determined by the rate at which drops of liquid are observed falling through a drip chamber. A miscalculation of flow rate can lead to many problems including extravasation, infusion phlebitis, infiltration, and even death. Gravity infusion of the parenteral solution is accomplished by suspending the solution container several feet above the patient and connecting the solution container to the venipuncture site via a disposable intravenous administration set which includes a drip chamber and flexible delivery tube.

Intravenous flow rates, usually expressed in: 1) number of drops; 2) cubic centimeters per minute (cc/min); or 3) milliliters per minute (ml/min), are commonly controlled by use of a roller clamp. U.S. Pat. No. 4,175,558 describes a roller clamp for collapsing the delivery tube to control the flow rate. The roller clamp is a simple, inexpensive, two-piece plastic device that progressively compresses the plastic tube of the intravenous administration set at a single point on the tube thereby occluding the tube to create a pressure drop across the restriction and a corresponding reduction in flow rate. The constancy of flow rates during use of such roller clamps is problematic due to cold flow or creep of the plastic tubing at the point of restriction, which causes the flow rate to decrease after setting. Another drawback is that the roller clamp requires electricity or battery power to function.

Continuous flow through the infusion system is usually necessary to ensure the proper delivery of the injected drugs into the patient and avoid accumulation of repeated doses within the IV tubing. However, administration of excess IV fluids is undesirable and frequently harmful. Even in otherwise healthy patients, inadvertently administered large volumes of IV fluids can result in urinary bladder distention and need for urethral catheterization during the surgery, or urinary obstruction post-operatively, all of which can cause increased hospital stays for the patient. In patients with heart or lung disease, the administration of excessive fluid volumes is a frequent cause of postoperative lung and cardiovascular dysfunction. This can result in congestive heart failure, pulmonary edema (i.e. swelling of the lungs) and difficulties in discontinuing mechanical ventilation (i.e. breathing machine) after surgery and anesthesia.

Historically, infusion systems can be difficult to control and the flow rate is cumbersome and inexact. Since these systems are capable of delivering high flow rates, failure to frequently assess and adjust the infusion rate using a roller clamp can easily result in administration of excess IV fluids. The risk of administering large fluid volumes is ever present also due to the deficiencies inherent in these infusion systems. For instance, the rate of drip formation has been found to be an inaccurate measure of flow rate because of the influence of temperature, fluid composition, orifice diameter, and orifice shape. Furthermore, the cold flow (i.e. "creep") in the tubing underlying the roller clamp can contribute to flow variation in excess of 15% over 45 minutes. When a vein collapses, critically high flow velocities occur, causing the distention of the vessels (produced by the downstream resistance) and paradoxically increase in the flow.

Veins are characterized by an opening pressure and by a small resistance to flow. Tissues behave as ordinary resistors with a resistance higher than that of veins. The opening pressure of tissue usually is no greater than that of veins, at least initially. In tissues, there is no obstructing pressure when there is no extravasation. However, as fluid is infused, opening tissue pressure rises. In response to these changes in flow rates, the clinician frequently has to check and adjust the roller clamp in order to properly adjust the IV flow so that the flow is continuous, keeping the veins open and assuring the delivery of administered medications and anesthetics, but not excessive to result in fluid overload or infusion of inappropriately large quantities of IV fluids.

Systems for administering intravenous liquids are described in U.S. Pat. Nos. 3,298,367 and 5,318,515. These patents generally describe a plurality of separate flow paths with each flow path having various flow characteristics. During operation and delivery of IV fluids both these patents would require a time consuming selection from a finite number of tubes and associated flow characteristics. Several flow rate regulators, including U.S. Pat. Nos. 3,877,428 and 5,019,055, have been introduced in recent years in attempts to overcome the aforementioned disadvantages associated with the use of conventional roller clamps and infusion procedures.

Information related to attempts to address these or similar problems can be found in U.S. Pat. Nos. 3,298,367; 3,877,428; 4,175,558; 5,019,055; 5,106,374; 5,318,515; 5,348,539; 6,428,505; and 8,257,337 as well as U.S. Patent Application Publication Nos. US 2010/0076413 and US 2012/0267275 and foreign Patent Application Nos. CA 1125134; EP 0217940; EP 0265261; and EP 0462213, for example. Various types of infusion systems for the controlled delivery of therapeutic agents, including some embodiments of the invention, can mitigate or reduce the effect of, or even take advantage of, some or all of these potential problems.

For at least the foregoing reasons, there's a legitimate need for infusion systems for the controlled delivery of therapeutic agents. It would be beneficial and desirable to provide a system that provides an infusion system that improves upon the conventional droplet monitoring technique (described above) and will, therefore, be familiar to and readily accepted by medical practitioners. It would also be advantageous to provide a simple method for the administration of intravenous fluid that is inexpensive to manufacture. Furthermore, it would be particularly helpful to provide an infusion system that permits the user to quickly begin a constant and/or predetermined flow rate in accordance with a prescribed therapy without the need to mix drugs, perform dosage calculations, or adjust the flow rate. It would also be advantageous, particularly for battlefield medicine, remote medicine, third-world health care and natural disaster situations, to provide an infusion system that does not rely on electricity or batteries to power the delivery infused drugs. Providing a self-contained, pre-packaged, sterilized kit containing an infusion system for the administration of drugs and/or fluids, would also offer convenient advantages.

BRIEF SUMMARY OF THE INVENTION

Various embodiments of the invention provide infusion systems, including for example systems which provide intravenous (IV) delivery of therapeutic agents, such as drugs. Certain embodiments of such systems utilize a chemical reaction or other pressure generation means to predictably drive a flow of therapeutic agents through a path and into a patient. More specifically, some embodiments of the present invention utilize an acid-base reaction or any other reaction that produces a gaseous substance to expand a drive balloon which, in turn, exerts a pressure on a separately-contained drug reservoir which, in turn, pushes a drug containing solution (hereinafter: "drug solution") from the reservoir into the flow path where the drug is ultimately delivered to the patient in a controlled and predetermined manner.

In accordance with one embodiment, the invention provides an infusion system for treating a patient comprising a housing, a therapeutic agent solution a reservoir containing the therapeutic agent solution, a drive balloon for providing a driving pressure to deliver the therapeutic agent solution, a flow path for controlled flow of the therapeutic agent solution and a delivery body for delivering the therapeutic agent solution to a delivery site in the body. The therapeutic agent solution comprises one or more therapeutic agents dissolved or otherwise contained in a liquid such as liquid water. The housing contains at least the reservoir and the drive balloon and will typically be rigid, (i.e. it does not appreciably expand from pressure exerted by the drive balloon). The housing may include a viewing window made from transparent materials for viewing one or more of the drug reservoir, drive balloon and a marker or gauge (e.g. a needle gauge) attached to one or both of the reservoir or drive balloon to let the user know how much therapeutic agent solution is left in the reservoir. The flow path includes a lumen, which has a first end and a second end. The first end is connected to the reservoir and the second end to the delivery body. The flow path may comprise a catheter or other hollow fluid delivery member known in the art. The expandable drive balloon is disposed within the rigid housing in at least a partially non-expanded state. The drive balloon includes a first section and a second section with each section separated by a releasable seal. The first section includes a liquid and the second section includes at least one reactant configured to chemically react with the liquid to produce a gas which expands the drive balloon. When the seal is released (e.g. by being pulled out), the liquid from the first section mixes with the reactant(s) in the second section to produce the gas which expands the drive balloon to exert a force on the reservoir to push the therapeutic agent solution into the flow path. The delivery body has a proximal portion and a distal portion. The proximal portion is coupled to the second end of the flow path and the distal portion includes a tissue penetrating distal end and is configured to deliver the therapeutic agent solution to the patient. In many embodiments, the delivery body may correspond to a butterfly needle or other hollow needle known in the art. In such embodiments, the butterfly or other needle will typically have a sterile removable sheath or cover, to maintain the sterility of the needle as well as protect against accidental needle sticks.

The reactants may include an acid and a base in amounts and ratios to produce a selected volume and pressure of gas. According to one or more embodiments the acid can be citric acid or acetic acid and the base can be sodium bicarbonate or sodium hydroxide which are configured to produce carbon dioxide gas. For these and related embodiments, the ratio of acid to be can be about 1:2 to respectively. Other embodiments contemplate other acid and bases in other ratios. The liquid may be water and various solutions thereof. In many embodiments, the gas corresponds to carbon dioxide, though other inert gases are also contemplated.

In various embodiments, the therapeutic agent solution can be delivered to the patient at a flow rate within a pre-determined selected range. According to one or more embodiments, the flow rate may be in a range between about 10 cc/min to about 500 cc/min. In preferred embodiments, the flow rate is in a range between about 0.5 cc/min to about 20 cc/min. The therapeutic agent has a usable quantity and the therapeutic agent may be delivered to the patient at a flow rate that remains within the desired range substantially throughout delivery of the useable quantity of the therapeutic agent. The delivery may be a hollow needle for intravenous or subcutaneous administration of the therapeutic agent to the patient. The delivery body may be a patch for transdermal administration of the therapeutic agent to the patient and the flow path may be a tube. As described above, in some embodiments, the housing may include a transparent window for viewing the reservoir and drive balloon in order to assess the volume of each, for example. A marker or gauge may be viewably positioned in the transparent window between the reservoir and the drive balloon. The marker may correspond to a needle or shape configured to indicate the relative amount of therapeutic agent remaining in the reservoir. The housing may be disposed at a height equal to or above the patient while the releasable seal may be a pinch valve, collar valve, weak-weld seal, pressure seal, pull tab or adhesive seal. The therapeutic agent may be a chemotherapy drug, anesthetic, analgesic, insulin, growth hormone, biological material, a saline or like solution, a fluid replacement solution, a nutritional solution, or a contrast dye, for example.

A second embodiment provides a delivery system for the intravenous delivery of a drug or other therapeutic agent at a predetermined flow rate from a reservoir to a patient. The system comprises the reservoir, a drug or other therapeutic agent solution contained in the reservoir, an expandable drive balloon for providing a driving pressure to deliver the therapeutic agent solution, a catheter for flow of the therapeutic agent solution, a hollow needle for insertion into the patient and a rigid housing for containing one or more components of the system. The rigid housing is fabricated from non-compliant materials and will typically contain at least the reservoir the drive balloon. It may include a viewing window made from optically transparent materials for viewing a gauge (e.g. a needle gauge) attached to one or both of the reservoir or drive balloon to let the user know how much solution is left in the reservoir. As described above the reservoir contains a solution of the drug or other therapeutic agent (the solution is sometimes referred to herein as a drug or therapeutic agent solution). In some cases, the solution need not contain a drug or therapeutic agent, but for example compounds such as saline to allow the solution to be used to replenish fluid and/or volume of the patient. The catheter has a first end and a second end with the first end connected to the reservoir. The expandable drive balloon is disposed within the rigid housing in at least a partially non-expanded state. The drive balloon includes a first section and a second section and each section may be separated by a releasable valve. The first section includes a liquid and the second section includes at least one reactant configured to chemically react with the liquid to produce a gas which expands the drive balloon. When the valve is released, the liquid from the first section can mix with the reactants(s) in the second section to produce the gas which expands the drive balloon to exert a pressure from the drive balloon to the reservoir to push the drug into the catheter. A hollow needle has a proximal end and a distal tip. The proximal end is coupled to the second end of the catheter and the distal tip is configured to be inserted through the skin of the patient to deliver the drug solution a blood vessel of the patient such as a vein or artery or a tissue site such as an intramuscular tissue site. The system may be self-priming.

A third embodiment provides a kit for the intravenous delivery of a drug to a patient. The kit may comprise one or more embodiments of the IV drug delivery system described above including foe example rigid housing containing a reservoir filled with the drug or other therapeutic agent solution and an expandable drive balloon. The balloon includes a first section containing a liquid and a second section containing at least one reactant. The sections are separated by a releasable seal. A catheter receives the drug when the seal is released and a hollow needle is connected to the catheter to deliver the drug to a blood vessel of the patient. A sterile package holds the housing, catheter and needle. Various embodiments of the kit are particularly useful for packaging and storing multiple components of the IV delivery system in a sterile environment while extending shelf life of key components of the system such as the drug solution, reactants and the reactant liquid.

In an exemplary body of a method of using the invention, a medical care provider would select an infusion system described herein having a desired drug or other therapeutic agent. For kit embodiments, be or she would open the packaging and remove the components of the system including the housing, delivery catheter and butterfly needle. The medical care provider can then place the housing on a hanging pole, on the patient's bedside or attach the housing to the patient (some embodiments of the system may include a strap for holding the housing against the patients arm, leg, or other portion of their body). The medical care provider can then pull out the releasable seal (e.g. by pulling on a tab or pin attached to the seal) to start the flow of drug solution and after observing that all air has been removed from the catheter inserts the needle into the arm or other area of the patient (e.g. the leg, etc.). In some embodiments, which include a bubble trap, or other bubble removal means, the medical care provider can insert the needle first and the pull out the releasable seal to start the flow of drug. The delivery of drug can be monitored using a marker or gauge attached to one of the drive balloon or reservoir and visible through the viewing window. Some embodiments may also include electronic volume and flow sensors for letting medical care providers know the flow rate and volume of therapeutic agent solution left in the reservoir. In particular embodiments, the sensors can be wirelessly coupled to a monitoring device such as a notepad, cell phone or other related device allowing the medical care provider to remotely monitor the flow rate of therapeutic agent solution and volume of therapeutic agent solution remaining in the revoir.

For a fuller understanding of the nature and advantages of the present invention, reference should be made to the ensuing detailed description taken in conjunction with the accompanying drawings. The drawings represent embodiments of the present invention by way of illustration. Accordingly, the drawings and descriptions of these embodiments are illustrative in nature and not restrictive.

DETAILED DESCRIPTION OF THE INVENTION

Various embodiments of the invention provide infusion systems that deliver therapeutic agents using a chemical reaction to predictably drive a flow of therapeutic agent through a flow path and into a patient. Certain embodiments utilize an acid-base reaction or any other reaction that produces a gaseous substance. The gas is produced and contained in an expandable drive balloon when the acid-base reactants are combined with a liquid. As the gas is produced, the drive balloon expands to exert pressure on a separately-contained drug reservoir which, in turn, pushes the drug from the reservoir into the flow path where the drug is ultimately delivered to the patient at a flow rate within a pre-determined range.

Figure 1:
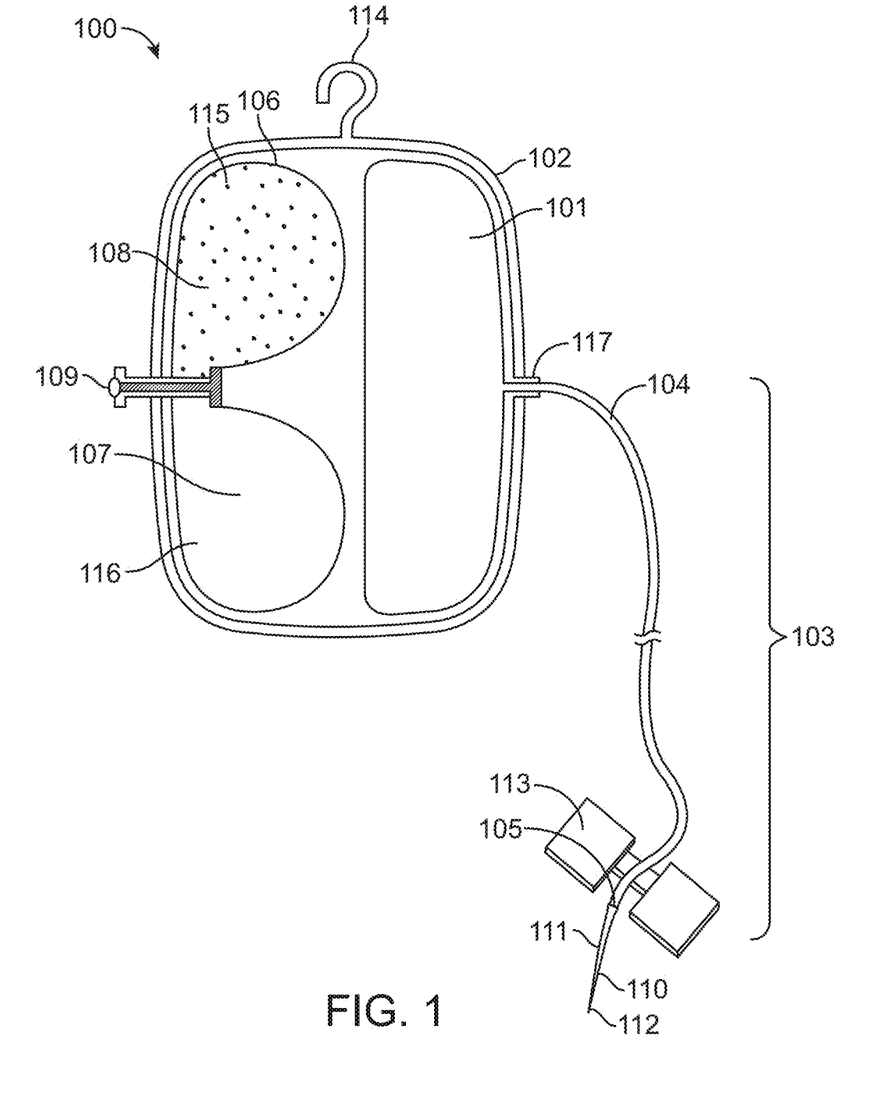
FIG. 1 is a perspective view of a system according to one embodiment of the invention.

FIG. 1 is a perspective view of a system according to one embodiment of the invention. Non-limiting, exemplary system claims are described further below. The particular system 100 of FIG. 1 includes a housing 102 with reservoir 101 and an expandable drive balloon 106 contained inside the housing. The housing 102 may be made of a non-compliant material or a rigid material including, but not limited to, plastic or metal. The housing 102 may contain an attachment device such as a hook 114, a ring 214 (FIG. 2) or the like to hang or otherwise suspend the housing at a selected height. Attachment device 114 may be configured to hang from one or more of a standard IV pole, hospital bed (e.g. the attached fittings) or the interior of an emergency response vehicle. This embodiment may be particularly advantageous in clinical settings such as chemotherapy wards or hospitals. The reservoir contains a therapeutic agent, such as a chemotherapy drug, anesthetic, analgesic, insulin, growth hormone, biological material (e.g. blood or plasma) or contrast dye, for example. The therapeutic agent may be either: 1) a crystalloid substance (prior to dissolution in a solution), such as 0.9% saline (i.e. normal saline), dextrose or Hartmann's Solution (i.e. Ringer's Lactate) or; 2) a colloidal substance such as blood products, hetastarch, gelatin derivatives dextran and the like. Of course, any other agent that provides beneficial treatment and/or therapy to a patient is also be contemplated for use in the system. The therapeutic agent may be pre-packaged in the reservoir thus avoiding the need to mix agents together.

The first section contains a liquid 116 (e.g. water) and the second section contains one or more reactants 115. The reactant(s) may also be pre-packaged in pre-determined amount(s) in order to produce a known volume of gas when they are combined in a chemical reaction. Those of skill in the art (e.g. familiar with basic laws of physics and chemistry) will also appreciate that it is possible to further calculate the pressure produced by the gaseous substance as well as the expansion of the drive balloon.

The drive balloon 106 is divided into first and second sections 107, 108, respectively, by a releasable seal 109. The seal 109 divides the first and second sections of the drive balloon so that the liquid 116 in the first section 107 does not contact the reactant(s) 115 contained in the second section 108 prior to activation (i.e. prior to releasing the seal). According to one or more embodiments, the seal 109 may be a pinch valve, collar valve, weak-weld seal, pressure seal, pull tab or adhesive seal. However, any mechanism that releasably separates the first and second sections 107, 108, respectively, of the drive balloon 106 is contemplated for use in the system.

The reservoir 101 of system 100 is connected to the first end 104 of the flow path 103 by a valve 117 (e.g. pinch valve). The length of the flow path 103 can vary in length but is desirably of sufficient length to connect the system to the patient without undue tension (e.g. to prevent stretching) or slack (e.g. to prevent tangling). Preferably, the flow path is a tube such as a cannula or catheter, for example. The flow path 103 may also have adhesive material 113 (i.e. tape) to hold the flow path securely to the patient. The second end of the flow path 105 connects to the proximal portion 111 of the delivery body 110. The delivery body 110 may be a hypodermic (i.e. hollow) needle with a distal portion 112 that can be inserted into a vein of the patient to deliver the therapeutic agent.

Figure 2:
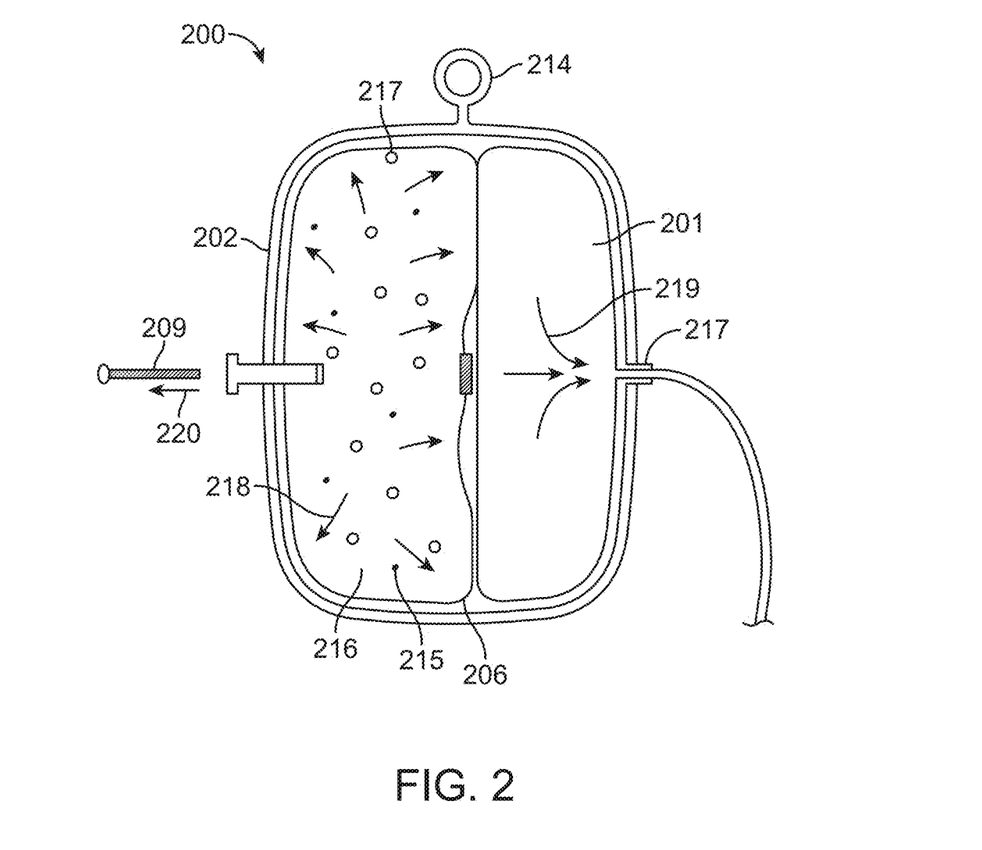
FIG. 2 is a side view of a system showing the seal released and the drive balloon expanding as it fills with gas in accord with one embodiment of the invention.

FIG. 2 is a view of an embodiment of system 200 showing the seal 209 released and the drive balloon 206 expanding as it fills with gas 217 in accord with one embodiment of the invention. The pinch valve has also been opened. The gas 217 may be carbon dioxide ($CO_2$) produced when acidic and basic reactants combine chemically. The ratio of acid to base may be about 1:2, respectively. The acid may include citric acid, hydrochloric acid, or acetic acid while the base may include sodium bicarbonate or sodium hydroxide, for example. Reacting a carbonate with an acid is a common way to produce carbon dioxide gas as generally shown in the exemplary chemical equation below:

$$Na_2CO_3 + 2HCl \rightarrow 2NaCl + \uparrow CO_2 + H_2O$$

These specific examples of reactants are relatively inexpensive, common and easy to produce. Many other reactants may be used which react to form a gaseous substance that expands the drive balloon to a volume sufficient to exert a pressure 218 against the non-compliant housing 202 and on the reservoir 201 to drive (i.e. push or squeeze) the therapeutic agent in a direction 219 into the flow path.

According to one or more embodiments, various dimensionless numbers known in the fluid dynamic and other engineering arts may be used to achieve a selected flow characteristic through the flow path. For example, Reynolds number (Re) provides a measure of the ratio of inertial forces to viscous forces and consequently quantifies the relative importance of these two types of forces for given flow conditions. For a flow path that is a tube, the Reynolds number is generally defined as:

$$Re = \rho v D_H / \mu = v D_H / \nu = Q D_H / \nu A$$

where:
- $D_H$ is defined herewith as the hydraulic diameter of the tube; its characteristic travelled length, L, (m);
- Q is defined as the volumetric flow rate ($m^3/s$);
- A is defined as the tube cross-sectional area ($m^2$);
- v is defined as the mean velocity of the therapeutic agent (SI units: m/s);
- $\mu$ is defined as the dynamic viscosity of the therapeutic agent (Pa·s or N·s/$m^2$ or kg/(m·s);
- $\nu$ is defined as the kinematic viscosity ($\nu = \mu/\rho$)($m^2/s$); and
- $\rho$ is defined as the density of the therapeutic agent (kg/$m^3$).

For flow paths such as squares, rectangular or annular paths, or the like, where the height and width are comparable, the characteristic dimension for internal flow situations is taken to be the hydraulic diameter, $D_H$, defined as:

$$D_H = 4A/P$$

where A is defined herewith as the cross-sectional area and P is defined as the wetted perimeter.

For a circular tube type flow path, including a standard 18G cannula, for example, the hydraulic diameter is exactly equal to the inside tube diameter, as can be shown mathematically.

Figure 6:
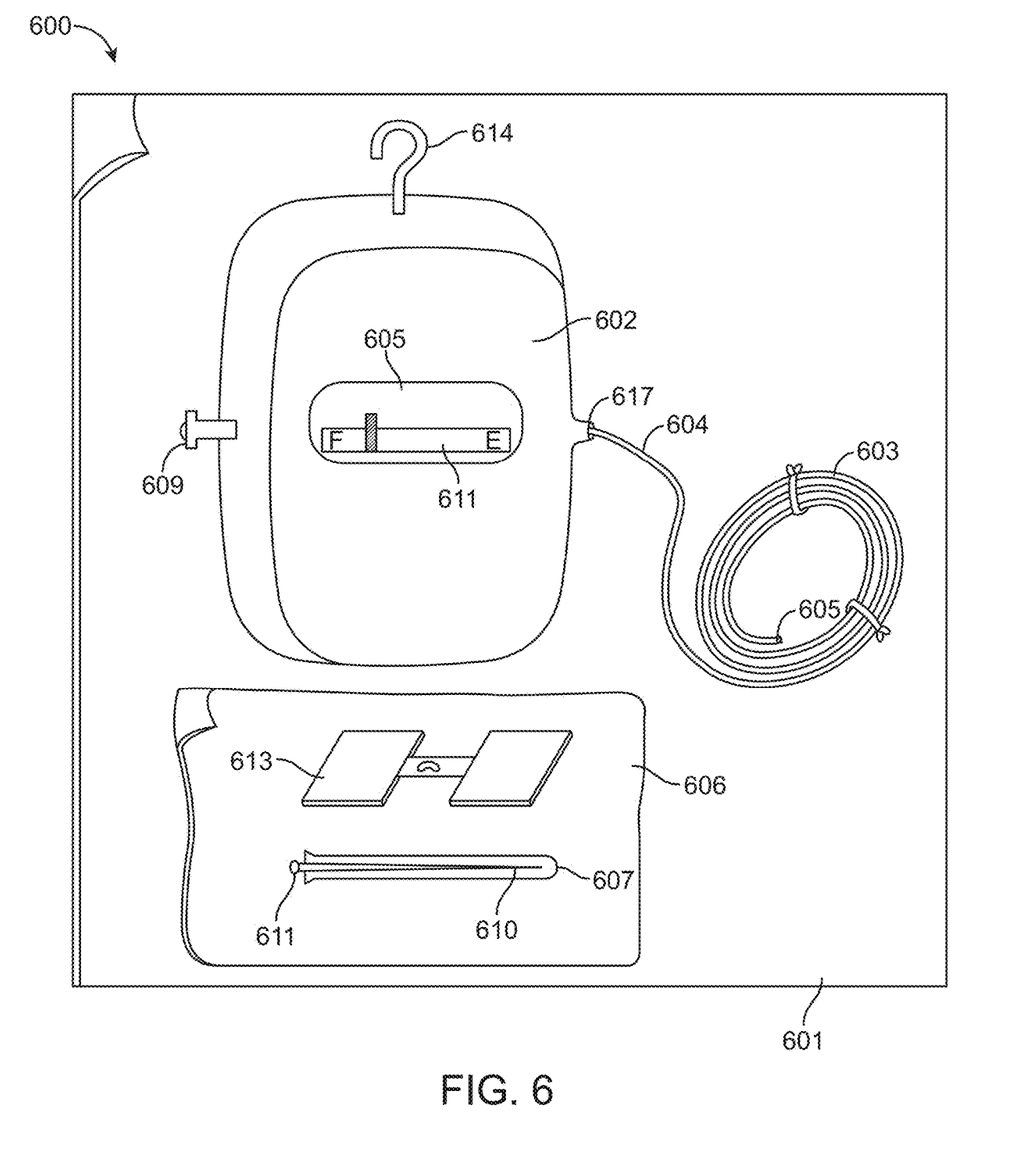
FIG. 6 is a kit according to an embodiment of the present invention.

In addition to flow rates described below, various embodiments of the inventions contemplate utilizing Reynolds number as a means to characterize flow through flow path. In various embodiments the Reynolds number of flow through the flow path can in a range of between about 10-4000. In preferred embodiments, the flow will be laminar and thus the Reynolds number will be below 2000. In specific embodiments the Reynolds number can be in a range of about 1-100, 100-500, 250-500, 500-1000, 1000-1500, 1000-2000 and 1-1000. These numbers can be achieved by selection of one or more of the above parameters comprising Reynolds number including, for example, the diameter of components in the flow path (e.g. catheter 603, and hollow needle 610), velocity and viscosity of the drug solution. Maintaining the Reynolds number within one of aforementioned ranges can be utilized to achieve one or more of the following: i) maintain a more constant and/or precise flow rate during infusion; ii) reduce fluidic resistance through the flow path; iii) reduce the pressure requirements to achieve a desired flow rate (which also reduces the height that the system is hung for hanging applications) iv) minimize bubble formation (e.g., due to cavitation); and v) reduce shear forces which may cause damage to infused platelets, or other colloidal substance. In particular embodiments, the Reynolds number is desirably maintained below 2000 (e.g. the transition from laminar to turbulent flow) and still more desirably, below 1000 as reduce the pressure requirements (and thus the amount of reactants) to achieve a desired flow rate through the flow path (this due to the reduced drag and fluidic resistance which occurs for Reynolds number below 2000). This in turn, allows for longer periods of infusion. Flow rates for a given pressure developed by the drive balloon may be calculated using standard fluid dynamic relations including shown below (also known as Poisell's law):

$$Q(\text{flow}) = \Delta P / R_f$$

where:
$\Delta P$ is defined as the pressure differential between the beginning and the end of the flow path (the beginning pressure corresponding to the pressure in the drive balloon).

$R_f$ is defined as the fluidic resistance of the flow path, and is equal the sum of the fluidic resistance R of the elements in the flow path including that of the catheter and the needle connected to the end of the catheter The fluidic resistance R of the elements in the flow path are given by the equation below:

$$R = \frac{8\eta\Delta x}{\pi r^4}.$$

where:
n is defined as the viscosity of the therapeutic agent solution;
$\Delta x$ represents the length of the component in the flow path; and
r is inner radius of the component in the flow path.

According to one or more embodiments, the flow rate can be selected by selection of the pressure of the drive balloon as well as the fluidic resistance of the components of the flow path (e.g. the catheter and needle). In specific embodiments, the fluidic resistance of the flow path is selected by selection of the inner diameter and length of each component. As shown in the above equation, since resistance varies by the inverse fourth power of inner radius, the selection of the inner gauge of the needle can have a significant impact on fluidic resistance particularly since the inner radius of the needle will often by smaller than that of the catheter. Accordingly, in many embodiments the choice of the needle gauge can be a controlling factor in determining flow rate. For some embodiments, depending on the gauge of the needle, the fluid resistance of the needle will predominate over that of the tubing, effectively allowing flow rate to be controlled mostly by selection of needle gauge. Accordingly, in these and related embodiments, use of small gauge needle (e.g. 18 or 20 gauge or higher) may allow use of several different sizes of catheters. In other embodiments, where larger needles are used, the resistance of the flow path and hence flow rate can be controlled by selection of the inner radius of the catheter and/or the combination of the selection of the inner radius of the catheter and the needle. In one or more embodiments, the system may include a computing means for determining a flow rate for a particular combination of needle gauge and catheter diameter and length. In various embodiments, the computing means may correspond to one or more software programs which may be run on a processor in a mobile device such as an Apple iPhone™ (or other smartphone device), an iPad™ (or other notepad device), or a computer device, such as a calculator included with embodiments of the system and/or kit described herein. The computing means may be configured to allow the user to select rate and then receive an output of a combination of needle and catheter dimensions. It may also take into account other factors described herein affecting flow rate, including for example, the pressure in the drive balloon, the viscosity of the drug solution and height that the drive balloon and reservoir are placed above or below the patient.

Some of the many examples of flow rates which may be delivered by various embodiments of the invention through selected gauges of cannulas (i.e. flow paths) are provided in the table below. It should be appreciated, however, that these flow rates are exemplary and a plethora of other flow rates and gauges may also be used depending on many variables and conditions.

Examples of Various Flow Rates Through Different Flow Path Sizes

| Flow Rate (cc/min.) | Flow Path Size (Gauge) |
| --- | --- |
| 250-360 | 14G |
| 130-220 | 16G |
| 75-120 | 18G |
| 40-80 | 20G |

According to one or more embodiments, the therapeutic agent may be delivered to the patient at a flow rate within a pre-determined range. The range of flow rates, including individual flow rate values, may be selected based on any number of criteria including the gauge and length of the flow path or the pressure of the drive balloon, for example. In particular embodiments, the range may be selected to deliver a selected volume of therapeutic agent (e.g. in the form of a therapeutic agent solution comprising one more drugs or other therapeutic agents) to be delivered over a selected period of time. For example, if it is desired to deliver 33.3 cc of solution over a ten minute period, then the flow path can be configured to have a flow rate of 3.33 cc/min.

According to one or more embodiments, the characteristics of the drive balloon can be selected to also control the flow rate. Such characteristics can include, for example, the size, shape, inflated pressure and compliance/elasticity of the drive balloon. The constant k of the expandable drive balloon is chosen so that the force exerted by the gas (after the seal and pinch valve are released) equals the hydrostatic force of the therapeutic agent exerted against the drive balloon. Assuming the housing is positioned at a height of 5 cm above the patient, the pressure may be generally estimated by:

$$P_h \rho g h (10^3 \text{ kg/m}^3)(10 \text{ m/sec}^2)(0.05 \text{ m}) = 500 \text{ kg/m-sec}^2$$

Where p denotes the density of the therapeutic agent and is assumed to be roughly the same density of water, at least for the sake of this example. The hydrostatic pressure $P_h$ and hydrostatic force $F_h$ are related by:

$$P_h = F_h/A$$

Were A denotes the area of the reservoir in contact with the drive balloon and is, for the sake of this exemplar, equal to $(3.6 \text{ cm})^2 = 13.0 \text{ cm}^3$. Hence:

$$F_h = P_h A = [500 \text{ kg/m-sec}^2](0.001.3 \text{ m}^2) = 6.5N$$

The force is expressed by:

$$F_s = kx$$

Where x denotes the distance that the reservoir has been compressed by the expanding drive balloon. Arbitrarily choosing x to be 1 cm and setting $F_s$ equal to $F_h$ yields:

$$K = 6.5N/0.01 \text{ m} = 650 N/M$$

Other factors affecting the flow rate, including for example, the diameter of the tubing (i.e. flow path), viscosity of the drug (i.e. therapeutic agent), rate of gas produced during the chemical reaction and various other considerations can be utilized alone or in combination to control flow rate. Those of skill in the art will appreciate various formulas that express and calculate representative flows of therapeutic agents to predictably deliver such agents to a patient at a rate within a pre-determined range. Accordingly, the equations and calculations described above are just a few of many examples and, as such, the subject invention is not necessarily limited to any specific equation or calculation.

According to one or more embodiment, the flow rate is preferably between about 10 cc/min. and 500 cc/min., with specific embodiments of 25, 50, 100, 200 300 and 400 cc/min. More preferably, the flow rate is between about 0.5 cc/min. and 20 cc/min. with specific embodiments of 1, 3, 5, 10 and 15 cc/min. Still other specific flow rates flow rate ranges are also contemplated. Regardless of the specific flow rate, it is preferred that the therapeutic agent is delivered to the patient at a flow rate that remains within the desired range substantially throughout the period of delivery of the agent. However, according to other embodiments, the flow rate may vary over a delivery period. For example, according to one embodiment, the flow rate can be configured to be higher during the beginning of a delivery period (e.g. the first minute or two) and then taper off so as to deliver an initial bolus dose of therapeutic agent followed up by a maintenance dose. Such variable flow rate embodiments can be achieved, for example, through the use of control valves or other like device.

Figure 3:
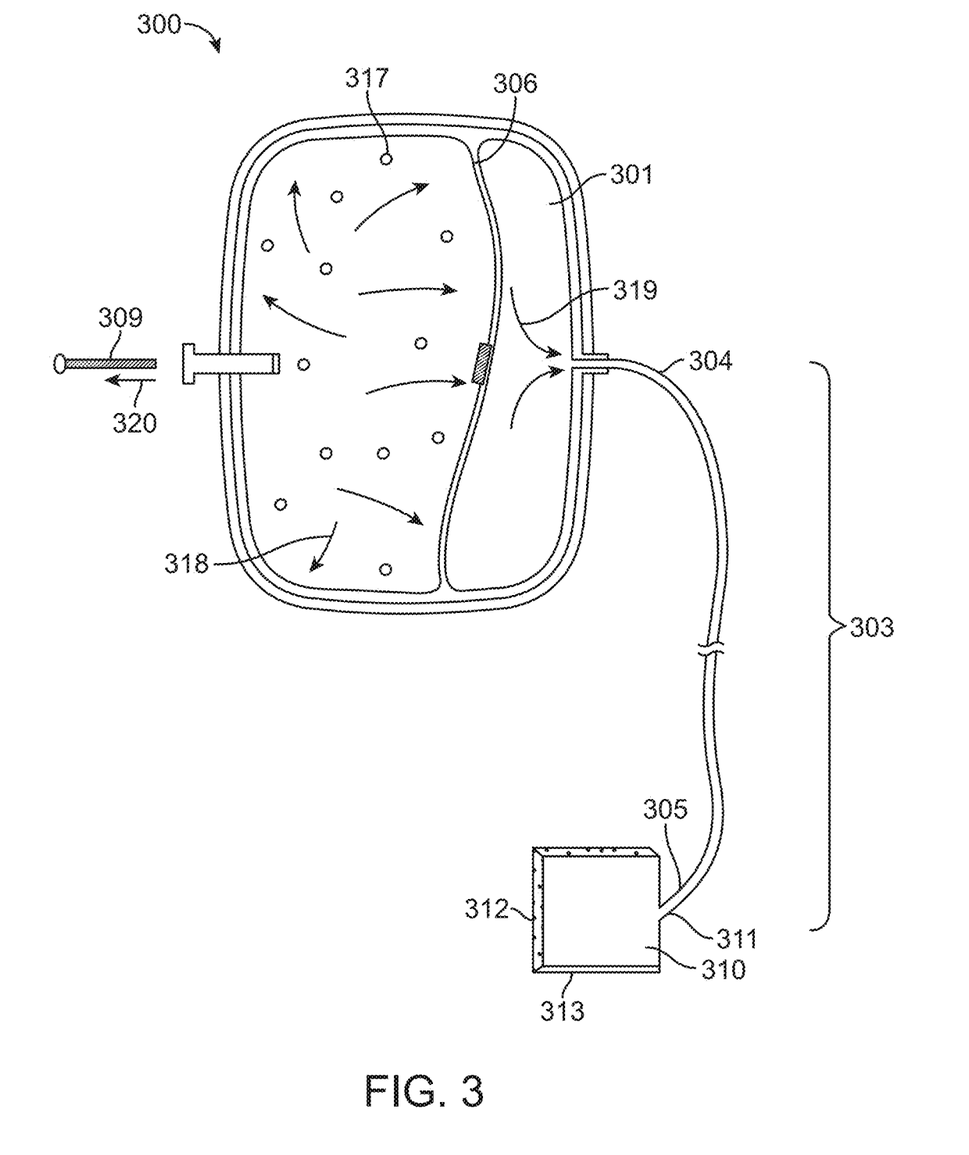
FIG. 3 is a perspective view of a system according to another embodiment of the invention.

FIG. 3 is a perspective view of a system 300 according to another embodiment of the invention. The therapeutic agent is flowing from the reservoir and into the first end 304 of the flow path 303. Briefly comparing the relative volumes of the reservoir and drive balloons shown in FIGS. 2 and 3, a general progression of the delivery of the agent can be visualized. FIG. 2 shows a reservoir 201 and drive balloon 206 that are relatively the same size (e.g. the volume of each occupying about 50% of the housing). As can be expected as the chemical reaction progresses toward completion, the volume of the drive balloon increases while the volume of the reservoir would be expected to decrease. This is generally depicted in FIG. 3 where the drive balloon 306 is now about 66% larger that the reservoir 301 as generally compared to FIG. 2, for example. This example is provided for comparative illustration purposes only as FIGS. 2 and 3 are not necessarily drawn to scale.

The second end of the flow path 305 connects to a proximal portion 311 of a transdermal wicking sponge or patch material 310. Adhesive 313 on the sponge helps secure the sponge to the patient's epidermis (i.e. skin) or mucous membrane to facilitate transdermal delivery of the agent to the patient in accordance with this particular embodiment. The absorption properties of the sponge will be generally commensurate with the flow rate so that the sponge will be maintained in a substantially moist condition to prevent the sponge from drying out or, alternatively, becoming too wet.

Figure 4:
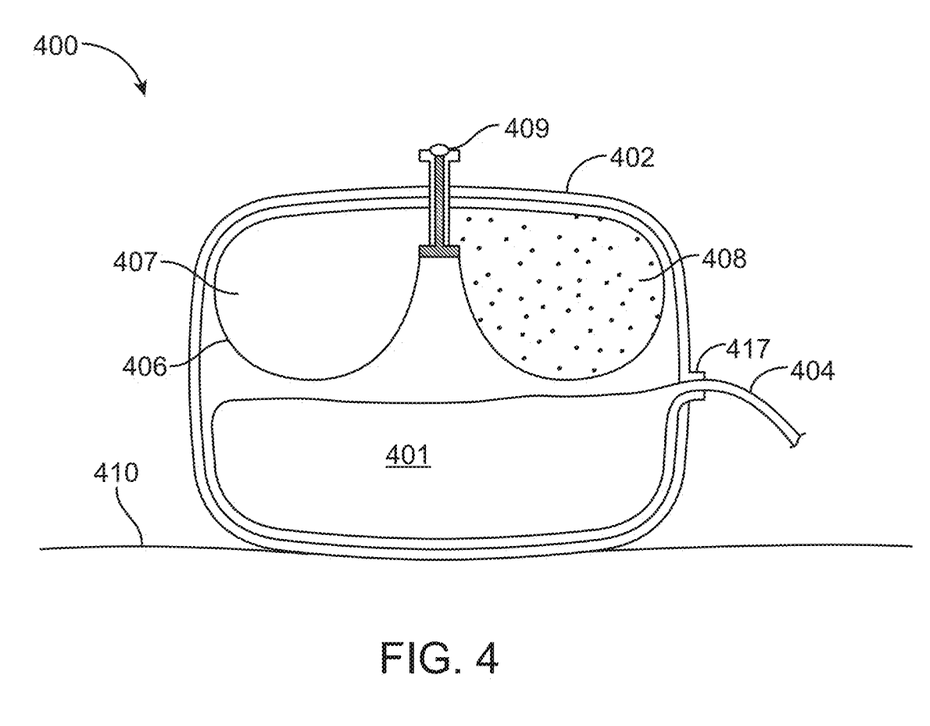
FIG. 4 is a side view of a system according to yet another embodiment of the invention.

FIG. 4 is a side view of a system according to yet another embodiment of the invention. In this embodiment (also known as the "vertically stacked arrangement"), the system rests on top of the patient 410 and, therefore, does not require suspending the system over or above the patient. Preferably, the system can lie on the patient's chest or stomach when the patient is lying in a supine or dorsal recumbent position. Alternatively, the system can be configured to rest on the patient's back when the patient is in a prone position. Many other arrangements of system placement relative to patient position are contemplated including resting the system on the patient's lap when the patient is seated, for example. The releasable seal may be facing upward or anywhere on the housing where access is readily available. The reservoir 401 is located nearest the patient and the expandable drive balloon 406 is located generally opposite the reservoir 401. The vertically stacked arrangement may be particularly advantageous during ambulatory care or other emergencies that require the services of first responders, such as field medics, emergency medical technicians (EMT), fire fighters and the like.

Figure 5A:
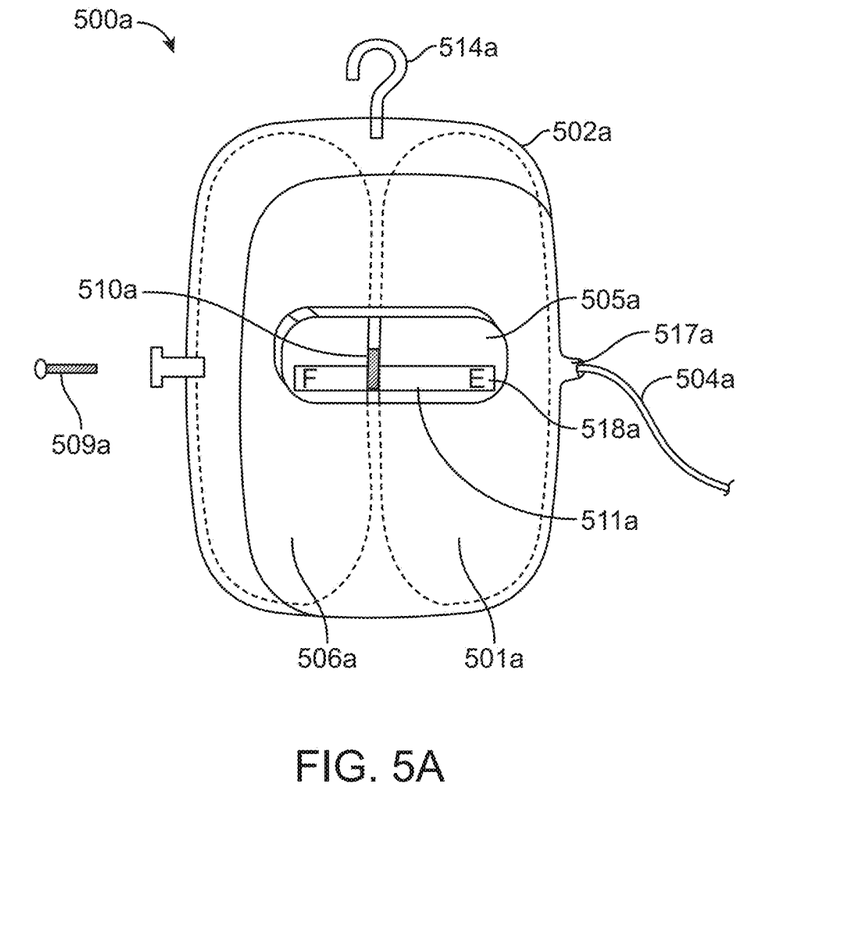
FIG. 5A is a side view showing a transparent window and a marker indicating the relative amount of therapeutic agent remaining in the reservoir according to an embodiment of the present invention.

FIG. 5A shows a side view of the system 500a including a transparent window 505a in the housing 502a for viewing the reservoir 501a and expandable drive balloon 506a. A marker 510a (i.e. meter or gauge) may be visible in the window to indicate the relative or actual amount of therapeutic agent remaining in the reservoir according to an embodiment of the present invention. The marker is positioned at between the reservoir 501a and drive balloon 506a and moves position along a scale 518a as the volume of the drive balloon expands and the volume of the reservoir decreases. The scale 518a may have any number of incremental markings or symbols or may simply include the letter "F" to indicate that the reservoir is "full" and the letter "E" to indicate that the reservoir is "empty", for example.

Figure 5B:
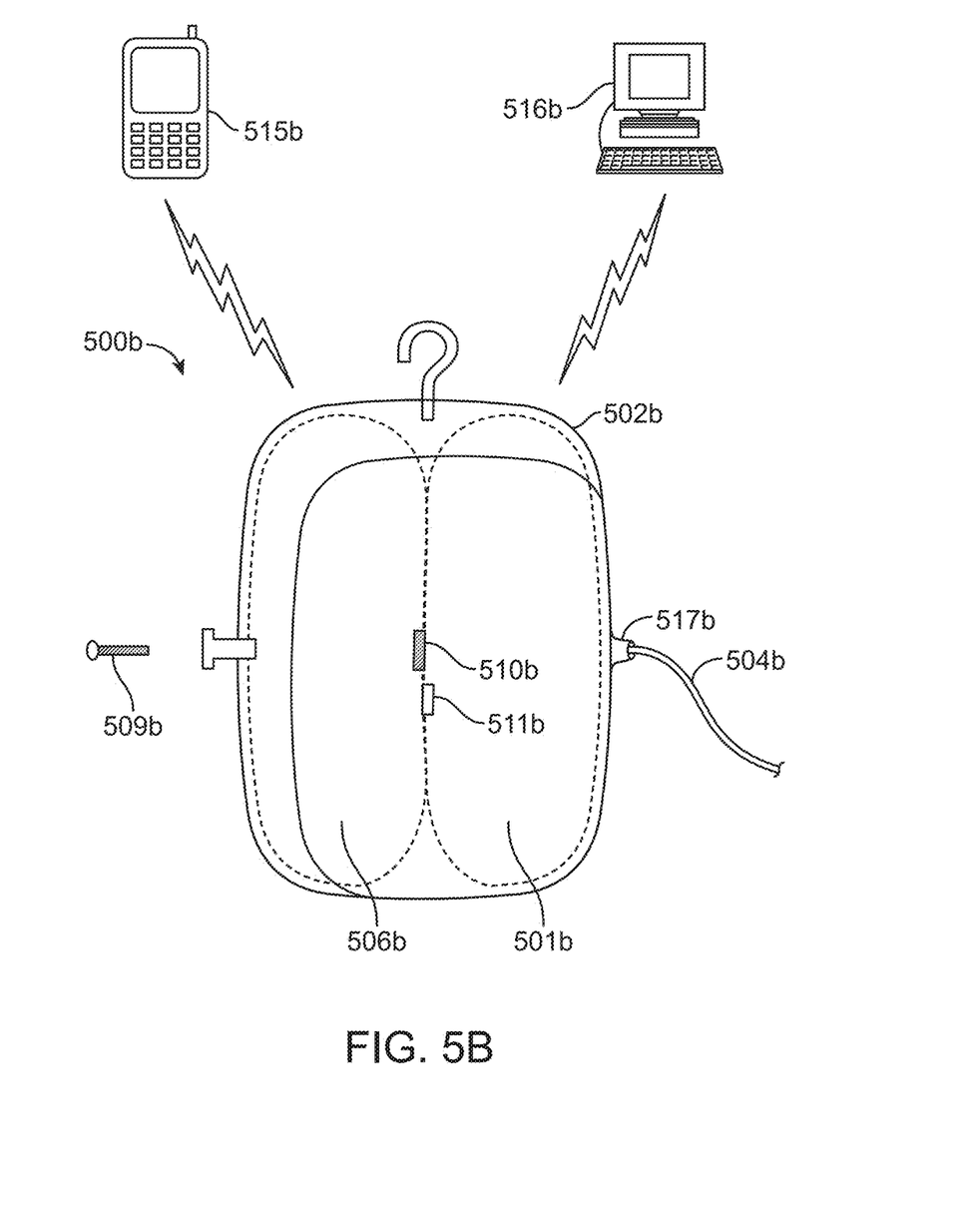
FIG. 5B is a side view showing sensors wirelessly coupled to electronic devices.

FIG. 5B shows a side view of the system of 500b including sensors 510b and/or 511b wirelessly coupled to one or more electronic devices such as a smart phone 515b or computer 516b, for example, to allow a medical care provider to remotely monitor the flow rate and/or pressure of the system 500b. In a clinical setting, the rates and total amount of delivered fluid/drug can be measured remotely from a nursing station, for example. In an emergency setting, the rates may be remotely monitored by emergency room personnel while the patient is transported via ambulance to the hospital, for example.

FIG. 6 is a self-contained sterile kit 601 for the intravenous delivery of a drug to a patient according to an embodiment of the present invention. A rigid housing 602 contains the reservoir filled with a drug and an expandable drive balloon. A catheter 603 receives the drug when the seal 609 is released (and the valve 617 is opened). A hollow needle 610, more preferably a hypodermic needle, a needle sheath 607 and adhesive material 613 are enclosed in a sterile package 606. The kit contains premeasured amounts of reactants, liquid and drug(s).

Figure 7A:
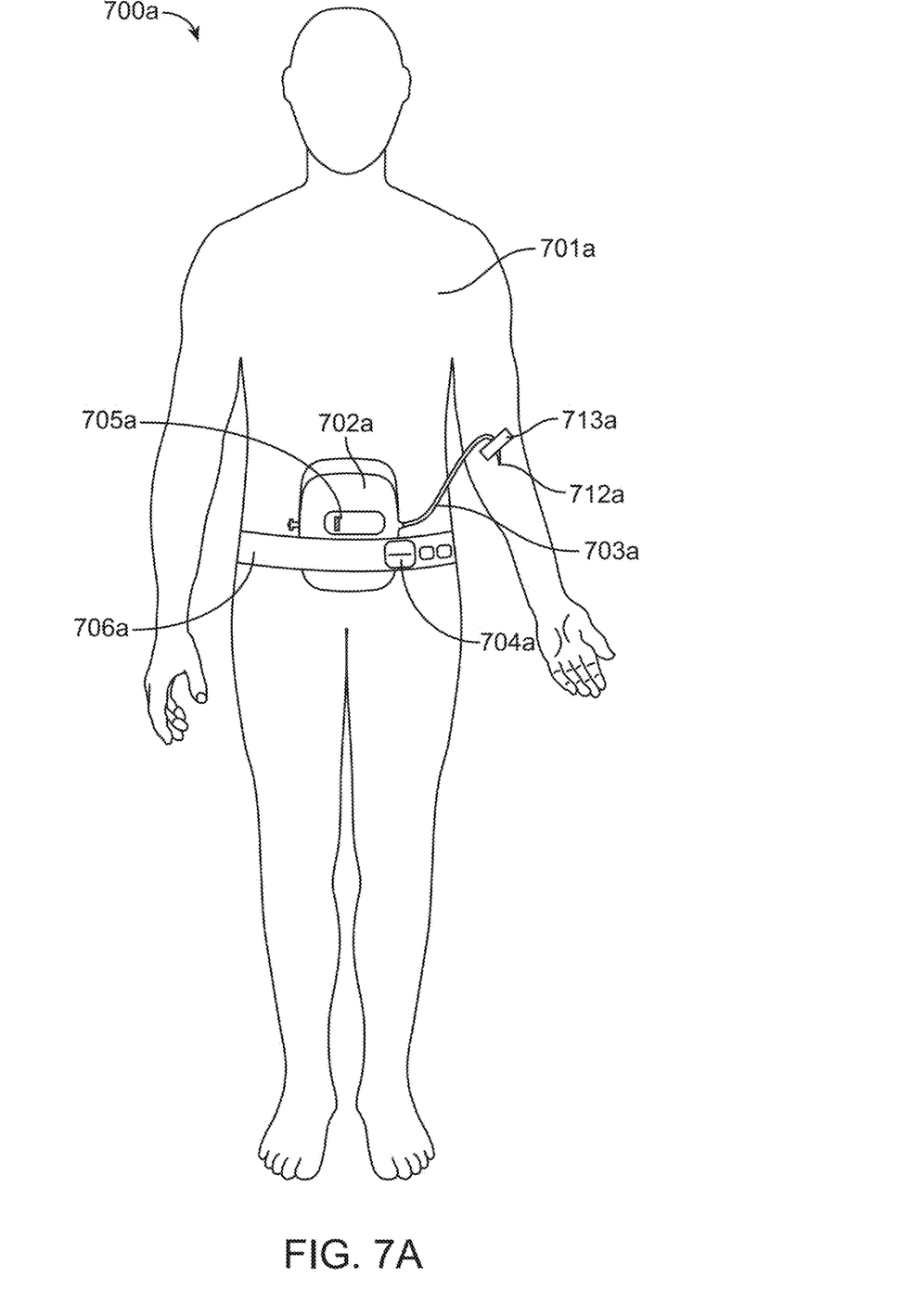
FIG. 7A is a perspective view of a system according to one embodiment of the invention.

FIG. 7A is a perspective view of a system 700a according to one embodiment of the invention. The system 700a may be secured to the patient by a belt, harness, or strap 706a to hold the housing 702a against the patient's body. The strap 706a can be securely fastened to the patient's arm, leg, waist or any other area of the patient's body with a buckle 704a, tie, or Velcro, for example. This embodiment may be particularly advantageous in an emergency setting where it may not be possible to suspend or hang the housing above the patient.

Figure 7B:
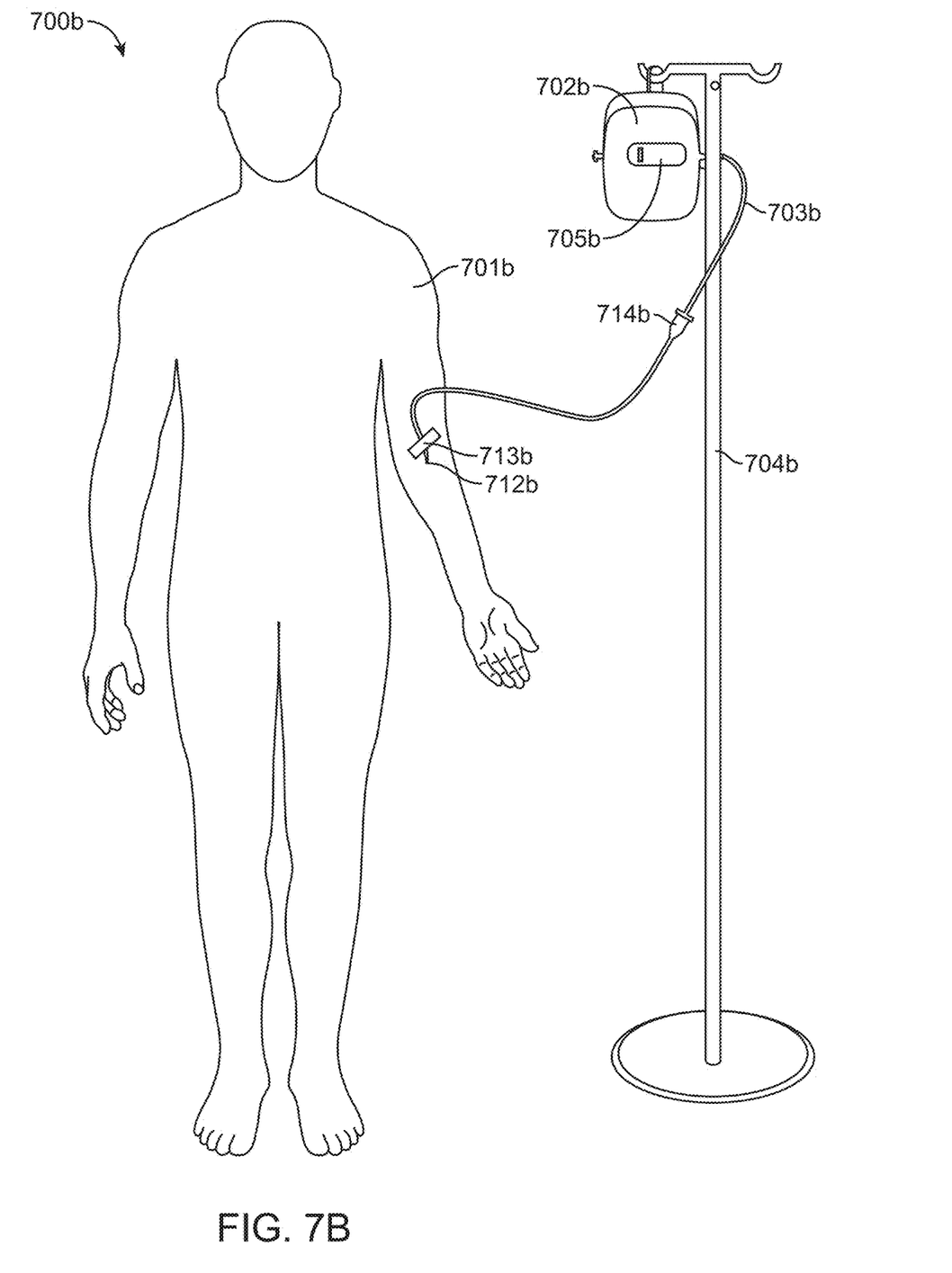
FIG. 7B is a perspective view of a system according to one embodiment of the invention.

FIG. 7B is a perspective view of a system 700b according to one embodiment of the invention. The system 700b may be configured to be suspended at a height above the patient in a nearby location such as a bedside hanger, hook, or IV pole 704b, for example. Also, the system may include a bubble trap 714b (or any of the embodiments described herein) which is configured to clear gas bubbles in the flow path and thus prevent the bubbles from entering the patient's vasculature.

The previously described embodiments of the subject invention may provide various advantages, including for example, providing infusion systems which provide for the IV delivery of drugs or fluids to a patient at a flow rate within a pre-determined range. Such embodiments provide new, useful, and non-obvious ways to effectively and efficiently deliver therapeutic agents.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments can be sized or otherwise adapted for various pediatric applications as well as various veterinary applications (e.g. canine, feline, equine, bovine, etc.).

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Also, the invention contemplates embodiments in which an element recited in the specification is excluded from that embodiment. Hence, the scope of the present invention is not limited to the specifics of the described embodiments, but is instead limited solely by the appended claims.

What is claimed is:

1. A system for delivering a therapeutic agent to a patient, the system comprising:
   a reservoir configured to contain a solution comprising the therapeutic agent;
   a rigid housing containing the reservoir, the rigid housing including a transparent window for viewing the reservoir and drive balloon;
   a marker viewably positioned in the transparent window between the reservoir and the drive balloon, the marker configured to indicate a relative amount of therapeutic agent solution remaining in the reservoir;
   a flow path having a first end and a second end, the first end coupled to the reservoir;
   an expandable drive balloon disposed within the rigid housing in at least a partially non-expanded state; wherein the drive balloon includes a first section and a second section, each section separated by a releasable seal;
   wherein the first section includes a liquid and the second section includes at least one reactant configured to chemically react with the liquid to produce a gas which expands the drive balloon;
   wherein when the releasable seal is released, the liquid from the first section mixes with the reactant(s) in the second section to produce the gas which expands the drive balloon to exert a pressure on the reservoir to push the therapeutic agent solution into the flow path;
   a delivery body having a proximal portion and a distal portion, the proximal portion coupled to the second end of the flow path and the distal portion configured to deliver the therapeutic agent solution to the patient; and
   wherein a fluidic resistance of the flow path and the pressure exerted on the reservoir are configured to deliver the therapeutic agent solution to the patient at a flow rate within a predetermined range.

2. The system of claim 1, wherein the reactant(s) includes an acid and a base in a ratio of about 1:2, respectively.

3. The system of claim 2, wherein the acid is citric acid or acetic acid and the base is sodium bicarbonate or sodium hydroxide.

4. The system of claim 1, wherein the liquid is water.

5. The system of claim 1, wherein the gas is carbon dioxide.

6. The system of claim 1, wherein the flow rate is between about 10 cc/min and 500 cc/min.

7. The system of claim 1, wherein the flow rate is between about 0.5 cc/min and 20 cc/min.

8. The system of claim 1, wherein the therapeutic agent solution has a usable quantity and wherein the therapeutic agent solution is delivered to the patient at a flow rate that remains within the predetermined range substantially throughout the delivery of the usable quantity of the therapeutic agent solution.

9. The system of claim 1, wherein the delivery body is a hollow needle for intravenous or subcutaneous administration of the therapeutic agent solution to the patient.

10. The system of claim 9, wherein a fluidic resistance of the hollow needle is configured to control the flow rate of the therapeutic agent solution.

11. The system of claim 1, wherein the delivery body is a patch for transdermal administration of the therapeutic agent solution to the patient.

12. The system of claim 1, wherein the flow path is a catheter.

13. The system of claim 1, wherein the rigid housing is disposed at a height equal to or above the patient.

14. The system of claim 1, wherein the releasable seal is a pinch valve, collar valve, weak-weld seal, pressure seal, pull tab or adhesive seal.

15. The system of claim 1, further comprising the therapeutic agent solution.

16. The system of claim 15, wherein the therapeutic agent solution comprises a chemotherapy drug, anesthetic, analgesic, insulin, growth hormone, biological material or a contrast dye.

17. A system for intravenous delivery of a drug to a patient, the drug delivered at a flow rate within a predetermined range, the system comprising:

a reservoir configured to contain a solution comprising the drug;

a rigid housing containing the reservoir, wherein the rigid housing includes a transparent window for viewing the reservoir and drive balloon;

a marker viewably positioned in the transparent window between the reservoir and the drive balloon, the marker configured to indicate a relative amount of therapeutic agent solution remaining in the reservoir;

a catheter having a first end and a second end; wherein the first end is connected to the reservoir;

an expandable drive balloon disposed within the rigid housing in at least a partially non-expanded state; wherein the drive balloon includes a first section and a second section, each section separated by a releasable valve; wherein the first section includes a liquid and the second section includes at least one reactant configured to chemically react with the liquid to produce a gas which expands the drive balloon, wherein when the releasable valve is released, the liquid from the first section mixes with the reactants(s) in the second section to produce the gas which expands the drive balloon to exert a pressure from the drive balloon to the reservoir to push the drug solution into the catheter; and a hollow needle having a proximal end and a distal tip; wherein the proximal end is coupled to the second end of the catheter and the distal tip is configured to deliver the drug solution to a blood vessel of the patient; and wherein the pressure exerted on the reservoir and a fluidic resistance of at least one of the catheter or the hollow needle are configured to deliver the drug solution to the patient at a flow rate within the predetermined range.

18. The system of claim 17, wherein the system is self-priming.

19. The system of claim 17, wherein a fluidic resistance of the hollow needle is configured to control the flow rate of the drug solution.

20. The system of claim 17, wherein the flow rate is between about 10 cc/min and 500 cc/min.

21. The system of claim 17, wherein the flow rate is between about 0.5 cc/min and 20 cc/min.

22. A kit for intravenous delivery of a drug to a patient, the kit comprising:

the system of claim 17; and a drug solution disposed in the reservoir.

23. The kit of claim 22, wherein the drug solution comprises a chemotherapy drug, anesthetic, analgesic, insulin, growth hormone, biological material or a contrast dye.

24. The kit of claim 22, further comprising a sterile package holding the rigid housing, catheter and hollow needle.

25. The kit of claim 22, further comprising a computing means for computing a flow rate through the catheter and hollow needle.

* * * * *